(12) United States Patent
Deister et al.

(10) Patent No.: US 11,166,800 B2
(45) Date of Patent: Nov. 9, 2021

(54) TISSUE GRAFTS WITH PRE-MADE ATTACHMENT POINTS

(71) Applicant: Axogen Corporation, Alachua, FL (US)

(72) Inventors: Curt Andrew Deister, Gainesville, FL (US); Jonathan Andrew Tinnemeyer, Newberry, FL (US); Kirk Michael Grayam, Bradenton, FL (US)

(73) Assignee: Axogen Corporation, Alachua, FL (US)

(*) Notice: Subject to any disclaimer, the term of this patent is extended or adjusted under 35 U.S.C. 154(b) by 158 days.

(21) Appl. No.: 16/381,860

(22) Filed: Apr. 11, 2019

(65) Prior Publication Data

US 2019/0314132 A1  Oct. 17, 2019

Related U.S. Application Data

(60) Provisional application No. 62/656,735, filed on Apr. 12, 2018.

(51) Int. Cl.
*A61F 2/00* (2006.01)
*A61L 27/54* (2006.01)
*A61L 27/38* (2006.01)

(52) U.S. Cl.
CPC ........ *A61F 2/0077* (2013.01); *A61L 27/3804* (2013.01); *A61L 27/54* (2013.01); *A61F 2002/0081* (2013.01)

(58) Field of Classification Search
CPC ............ A61B 17/1128; A61B 17/1146; A61B 2017/1132; A61F 2/0063; A61F 2/0077;
(Continued)

(56) References Cited

U.S. PATENT DOCUMENTS 4,586,504 A * 5/1986 de Medinaceli ... A61B 17/1128
606/152
5,972,371 A * 10/1999 Gilchrist ............... A61L 31/146
424/426

(Continued)

FOREIGN PATENT DOCUMENTS

EP  3162304 A1  3/2017

OTHER PUBLICATIONS

International Search Report issued in PCT Application Serial No. PCT/US2019/027046 dated Jul. 2, 2019.

(Continued)

*Primary Examiner* — Ryan J. Severson
(74) *Attorney, Agent, or Firm* — Bookoff McAndrews, PLLC

(57) ABSTRACT

The present disclosure pertains to membranous tissue grafts comprising one or more pre-made attachment points. The one or more pre-made attachment points may include pre-made markings and/or pre-made suture holes. The membranous tissue grafts can be in the form of a tube. The membranous tissue grafts can also be rectangular in shape and can be used in a nerve repair by wrapping the severed or damaged nerve. In some embodiments, the membranous tissue grafts are suitable for repairing severed nerves that have a short gap or no gap with a gap of less than 5 mm between the severed stumps. Accordingly, methods are provided for repairing a damaged or severed nerve by implanting the membranous tissue grafts on to the damaged or severed nerve.

21 Claims, 12 Drawing Sheets

(58) Field of Classification Search
CPC ............... A61F 2/04; A61F 2002/0081; A61F 2230/0019; A61F 2230/0069; A61L 2430/32
See application file for complete search history.

(56) References Cited

U.S. PATENT DOCUMENTS

| | | | | |
|---|---|---|---|---|
| 6,716,225 | B2* | 4/2004 | Li | A61B 17/1128 600/36 |
| 7,172,625 | B2* | 2/2007 | Shu | A61F 2/2409 128/898 |
| 7,198,799 | B2* | 4/2007 | Mueller | A61B 17/1128 424/426 |
| 7,410,497 | B2* | 8/2008 | Hastings | A61B 5/445 623/1.11 |
| 7,744,612 | B2* | 6/2010 | Blain | A61B 17/025 606/152 |
| 7,780,708 | B2* | 8/2010 | Morris | A61B 17/7059 606/279 |
| 7,878,969 | B2* | 2/2011 | Chu | A61F 2/0063 600/30 |
| 8,100,963 | B2* | 1/2012 | Roth | A61F 2/915 623/1.42 |
| 8,262,692 | B2* | 9/2012 | Rudakov | A61B 17/12113 606/200 |
| 8,585,753 | B2* | 11/2013 | Scanlon | A61L 31/10 623/1.42 |
| 9,039,649 | B2* | 5/2015 | Neisz | A61F 5/0079 604/8 |
| 9,345,486 | B2* | 5/2016 | Zhang | A61L 27/26 |
| 9,345,577 | B2* | 5/2016 | Vanleeuwen | A61B 17/1778 |
| 9,402,868 | B2* | 8/2016 | Muir | A61L 27/227 |
| 9,839,507 | B2* | 12/2017 | Harms | B29C 43/203 |
| 10,363,041 | B2* | 7/2019 | Yu | A61L 27/50 |
| 10,792,391 | B2* | 10/2020 | Yuan | A61L 27/56 |
| 2003/0028204 | A1* | 2/2003 | Li | A61L 31/044 606/152 |
| 2004/0010275 | A1* | 1/2004 | Jacobs | A61B 17/08 606/153 |
| 2004/0015232 | A1 | 1/2004 | Shu et al. | |
| 2004/0034376 | A1* | 2/2004 | Wildes | A61F 6/20 606/153 |
| 2005/0177162 | A1* | 8/2005 | McLeod | A61B 17/842 606/70 |
| 2007/0010831 | A1* | 1/2007 | Romero-Ortega | A61L 31/146 606/152 |
| 2009/0018655 | A1* | 1/2009 | Brunelle | A61L 27/24 623/13.19 |
| 2010/0234863 | A1* | 9/2010 | Zhang | A61L 27/26 606/152 |
| 2013/0324904 | A1* | 12/2013 | Neisz | A61F 5/0076 604/8 |
| 2013/0337549 | A1* | 12/2013 | Muir | A61L 27/3683 435/268 |
| 2014/0343675 | A1* | 11/2014 | Vanleeuwen | A61F 2/40 623/14.12 |
| 2015/0057762 | A1* | 2/2015 | Harms | B29C 43/18 623/23.74 |
| 2017/0119396 | A1* | 5/2017 | Deister | A61B 17/1128 |
| 2017/0172578 | A1* | 6/2017 | Yu | A61B 17/1128 |
| 2018/0071526 | A1* | 3/2018 | Novak | A61N 1/326 |
| 2019/0022276 | A1* | 1/2019 | Yuan | A61B 17/1128 |
| 2019/0314132 | A1* | 10/2019 | Deister | A61L 27/54 |

OTHER PUBLICATIONS

Nectow et al., "Biomaterials for the Development of Peripheral Nerve Guidance Conduits," Tissue Engineering Part B, Sep. 23, 2011, vol. 18, No. 1, pp. 40-50.

* cited by examiner

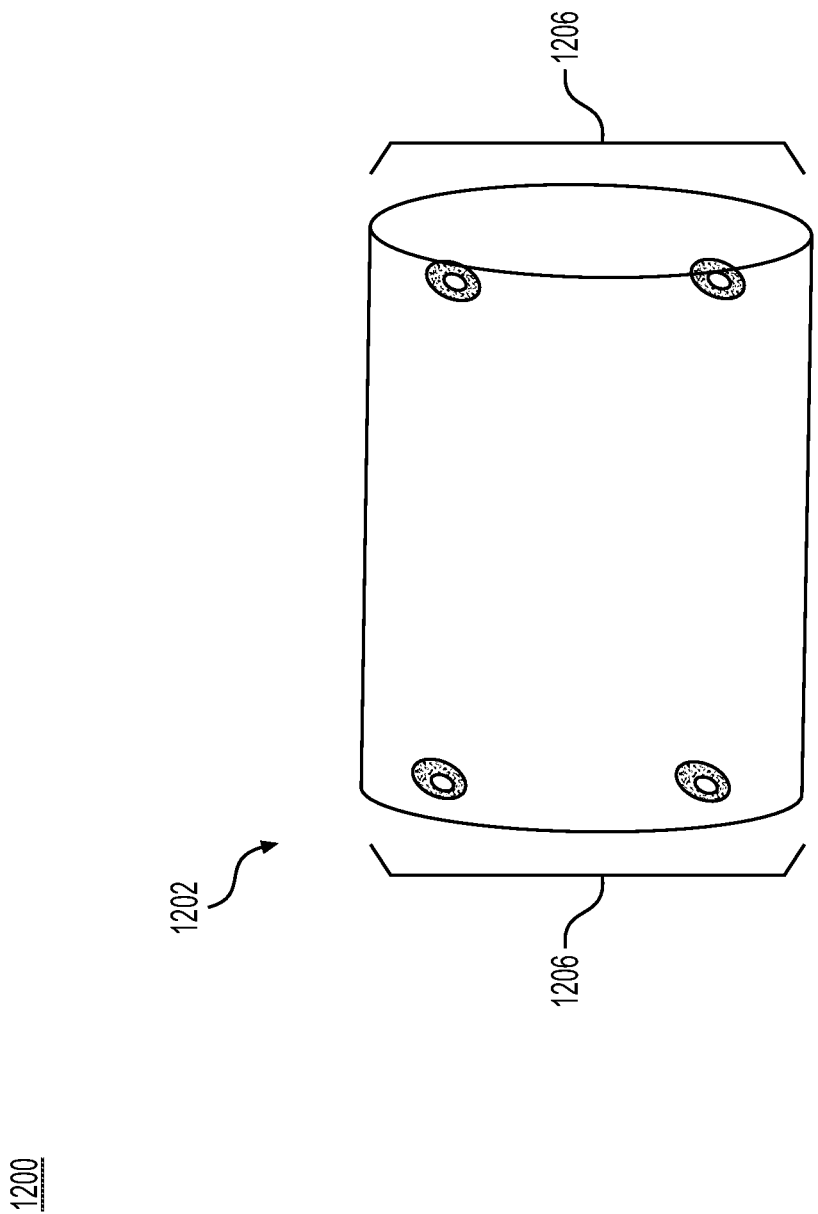

TISSUE GRAFTS WITH PRE-MADE ATTACHMENT POINTS

RELATED APPLICATION

This application claims the benefit of U.S. Provisional Application No. 62/656,735, filed on 12 Apr. 2018; the contents of which are incorporated herein by reference.

TECHNICAL FIELD

This application relates to tissue grafts and, more particularly, to tissue grafts with pre-made attachment points.

BACKGROUND

Membranous tissue grafts are often used as a matrix for tissue repair or regeneration, particularly, soft tissue repair or regeneration. Typically, such tissue grafts are glued or sutured onto an injured tissue. Once implanted, the tissue graft can protect the injured tissue and support growth and repair of the tissue. The tissue graft can even be incorporated into the repaired tissue and become a part of the repaired/regenerated tissue.

Certain membranous tissue grafts are relatively mechanically robust and provide mechanical properties appropriate for a reinforcing soft tissue graft. Suture materials, especially needles, appropriate for microsurgical use in nerve repair may not always be appropriate for securing a mechanically robust tissue-based membrane. For instance, a needle with a larger diameter and a cutting edge may be needed to prevent bending of the needle in the membranous tissue graft. Use of such a needle may be disadvantageous, however, as the microsurgical work might better be performed using a thinner, taper point needle, which may cause less tissue trauma during use.

Certain other membranous tissue grafts have relatively weak mechanical properties to facilitate use as a cushioning or lubricating material. In such cases, the grafts' properties may be such that tears or rips occur, mainly caused by placement of a suture. Such tears or rips can easily propagate through the material and cause a mechanical failure.

Certain membranous tissue grafts can be formed into tubes or conduits, or other forms for supporting and reinforcing microsurgical repairs such as repairing injured nerves. Due to the specialized needs of microsurgical repairs, suture and suture needle parameters can be critical to the surgical procedure. Therefore, membranous tissue grafts are desirable that can be sutured with any suture type without damage to the graft, the suture needle, or the underlying tissue, and while retaining the bulk mechanical properties of the graft.

SUMMARY OF DISCLOSURE

The subject disclosure provides membranous tissue grafts designed to avoid, reduce, or minimize difficulty in suturing. In some embodiments, a membranous tissue graft may include one or more pre-made attachment points.

One or more of the following features may be included. The membranous tissue graft may have a thickness of between 25 microns and 3 millimeters. The membranous tissue graft may comprise a natural material. The natural material may be selected from porcine small intestine submucosa, amniotic/chorionic membrane, reconstituted denatured collagen, collagen, elastin, thrombin, fibronectin, starches, poly(amino acid), gelatin, alginate, pectin, fibrin, oxidized cellulose, chitin, chitosan, tropoelastin, hyaluronic acid, fibrin-based materials, collagen-based materials, hyaluronic acid-based materials, glycoprotein-based materials, cellulose-based materials, silks, and combinations thereof. The membranous tissue graft may comprise a synthetic material. The synthetic material may be selected from silicone, expanded polytetrafluoroethylene (ePTFE), polyethylene tetraphthlate (Dacron), polyurethane aliphatic polyesters, poly(amino acids), poly(propylene fumarate), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and blends thereof. The membranous tissue graft may include one or more bioactive components that facilitate repair of a damaged tissue. The one or more pre-made attachment points may include one or more pre-made suture holes. The one or more pre-made attachment points may be disposed towards a periphery of the membranous tissue graft. The membranous tissue graft may be in the form of a tube and the one or more pre-made attachment points may be disposed along edges at two ends of the tube. The membranous tissue graft may be rectangular and the one or more pre-made attachment points may be disposed along two opposite sides of the rectangular membranous tissue graft and may be absent along the other two sides. The one or more pre-made attachment points may be disposed along the edge of the membranous tissue graft at a distance from the edge of about 0.5 millimeters to about 10 millimeters.

The one or more pre-made attachment points may include one or more markings disposed on the membranous tissue graft and configured to increase the visibility of the one or more pre-made attachment points. The membranous tissue graft may be rectangular and the one or more markings may be disposed along two opposite sides of the rectangular membranous tissue graft and may be absent along the other two sides. The one or more markings may be disposed along the edge of the tissue graft at a distance from the edge of about 0.5 millimeters to about 10 millimeters. The one or more markings indicate an orientation of the membranous tissue graft. The one or more markings may be positioned to assist a user in placement of tissue at a measured distance within the membranous tissue graft. The one or more pre-made attachment points may include one or more pre-made suture holes and one or more markings.

In another embodiment, a method of repairing a damaged and/or severed nerve is provided. The method may include implanting a membranous tissue graft with one or more pre-made attachment points to the damaged and/or severed nerve. The damaged and/or severed nerve may have a gap in the range of about 0 millimeters to about 5 millimeters.

The details of one or more example embodiments are set forth in the accompanying drawings and the description below. Other possible example features and/or possible example advantages will become apparent from the description, the drawings, and the claims. Some embodiments may not have those possible example features and/or possible example advantages, and such possible example features and/or possible example advantages may not necessarily be required of some embodiments.

BRIEF DESCRIPTION OF THE DRAWINGS

FIG. 12 shows an example of implementation of the membranous tissue graft of the present disclosure in a nerve repair connector tissue graft.

DETAILED DESCRIPTION

Figure 1:
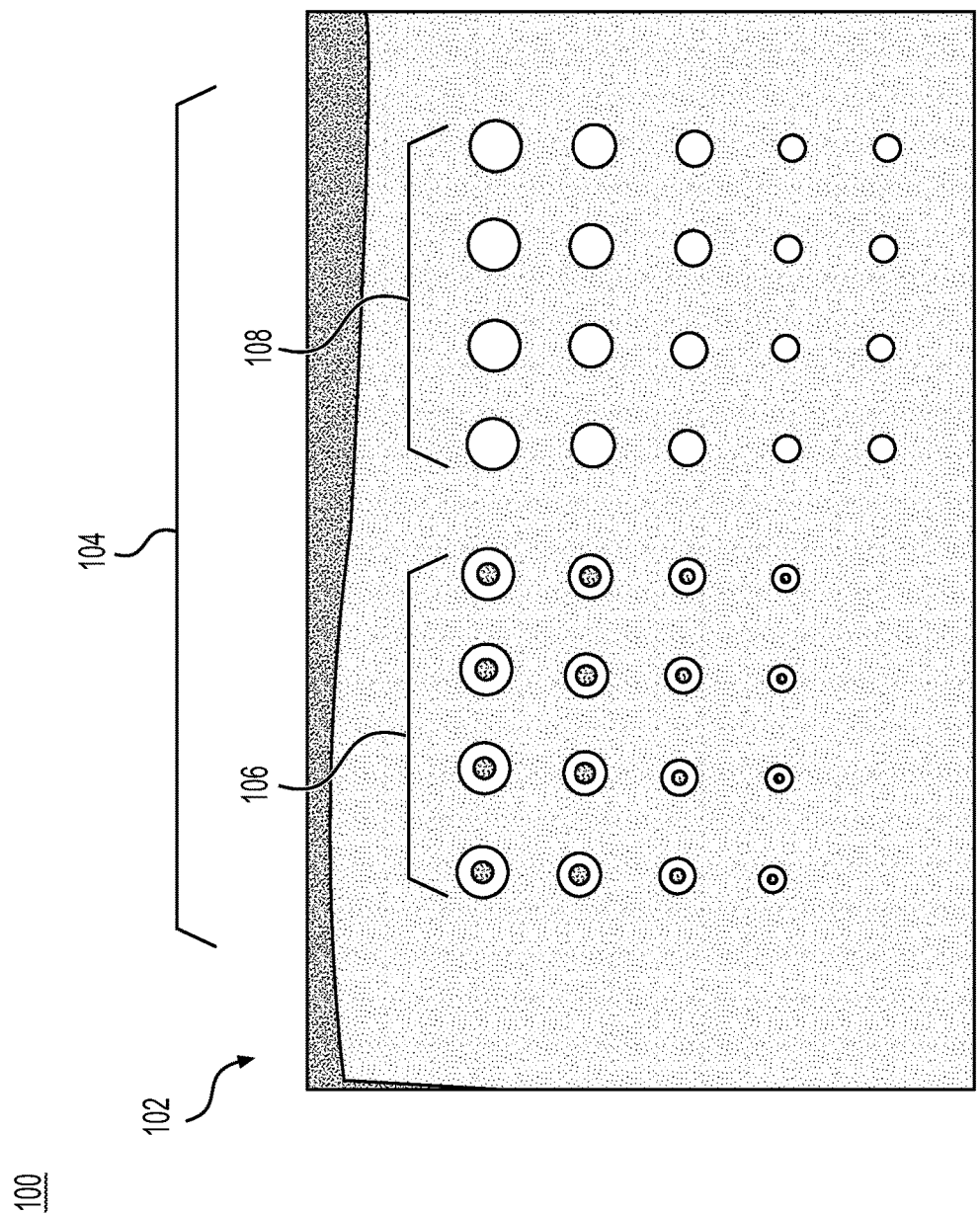
FIG. 1 shows an example of one or more pre-made attachment points (e.g., one or more pre-made etchings and one or more pre-made suture holes) in an exemplary membranous tissue graft of the present disclosure.
Figure 2:
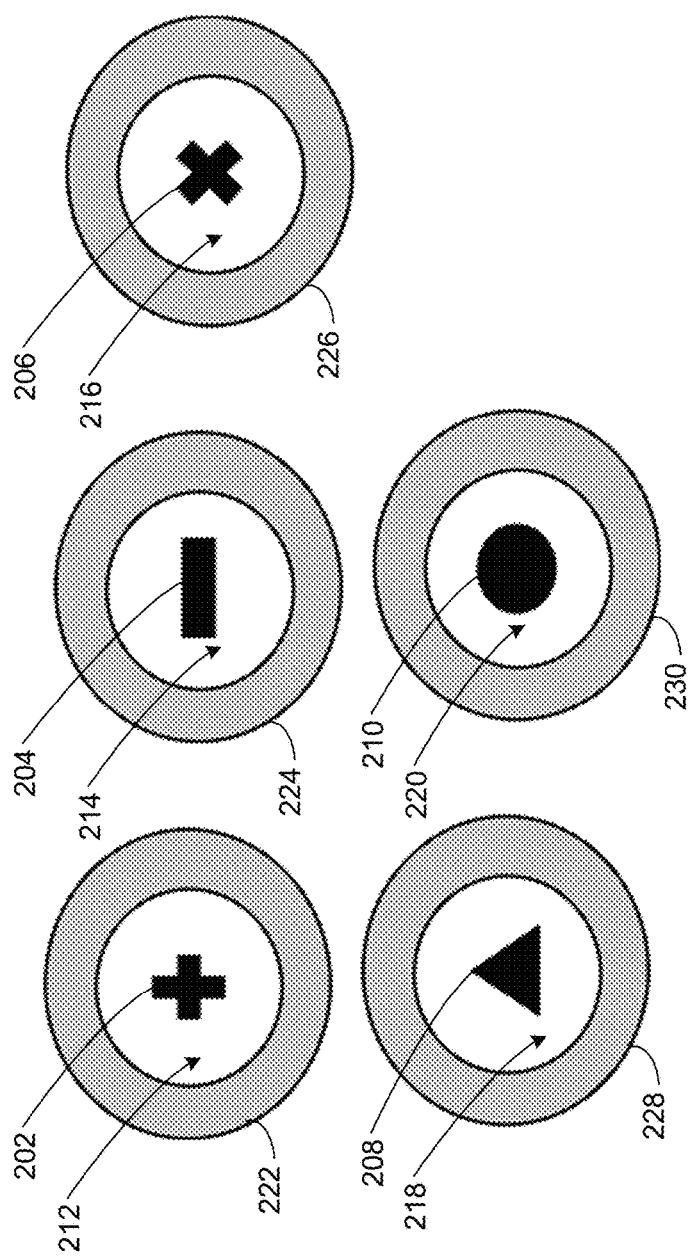
FIG. 2 shows exemplary shapes and forms of suture holes. In each embodiment, the solid fill towards the center indicates a hole or a cut. The white region surrounding the hole indicates optional etching. Further, the shaded region surrounding the white region indicates an optional reinforced region.

In some particular example embodiments, the present disclosure may provide membranous tissue grafts comprising one or more pre-made attachment points (e.g., pre-made suture holes and surrounding features to increase visibility and/or reinforce the suture point).

In certain example embodiments, the tissue graft of the present disclosure may be in the form of a tube that is designed for implantation onto an injured tissue, such as injured nerve. In other embodiments, the tissue graft of the present disclosure may be in the form of a sheet designed for implantation onto the surface of an injured tissue, such as injured nerve.

Suture holes in the tissue grafts of some embodiments consistent with the present disclosure may facilitate suturing of the tissue grafts to an injured tissue, such as an injured nerve. Etching or other methods can be used to increase the visibility of the suture holes.

In some example embodiments, the tissue grafts of the present disclosure may be suitable for repairing injured nerves, such as severed nerves that have no gap or a gap of e.g., less than about 5 mm between the severed nerve stumps. Accordingly, methods of using the tissue grafts of the present disclosure are also described. These methods include, for example, methods of repairing a damaged or severed nerve by implanting the tissue grafts of the present disclosure onto the damaged or severed nerve. Tissue grafts consistent with the present disclosure may be utilized for other purposes.

Tissue grafts are typically glued or sutured to a damaged tissue. A membranous tissue graft and/or an injured tissue can be damaged because of suturing-related issues, such as, bending or dulling of the needle by a relatively mechanically-tough tissue-based membrane causing more extensive trauma to the underlying nerve tissue, tearing while suturing or tearing because of pressure exerted on the graft after suturing, etc. In particular embodiments, the present disclosure may provide membranous tissue grafts comprising one or more pre-made attachment points (e.g., suture holes and/or markings such as etching designed to increase visibility of the suture holes) to assist individuals such as medical professionals when repairing tissue(s).

Referring to the examples of FIGS. 1-12 and in some embodiments, "membranous tissue graft" as used herein may generally refer to a relatively thin graft suitable for implantation into a subject in a surgical procedure or other medical procedure. The membranous tissue graft (e.g., membranous tissue graft 102) can be made of any of a variety of synthetic and/or natural materials. The membranous tissue graft (e.g., membranous tissue graft 102) can have a thickness of, for example, from about 25 microns to 3 mm, 100 microns to 2.75 mm, 200 microns to 2.5 mm, 300 microns to 2 mm, or 500 microns to 1.5 mm. In one embodiment the thickness is about 100 microns. However, it will be appreciated that the membranous tissue graft may have any thickness within the scope of the present disclosure.

In some embodiments, membranous tissue grafts (e.g., membranous tissue graft 102) can be comprised of a natural material, such as porcine small intestine submucosa, amniotic/chorionic membrane, or reconstituted denatured collagen. Membranous tissue grafts (e.g., membranous tissue graft 102) can also be made from a synthetic material. In preferred embodiments, the membranous tissue graft (e.g., membranous tissue graft 102) may be non-immunologic to the recipient.

Synthetic materials suitable for use in the membranous tissue grafts include, but are not limited to, silicone membranes, expanded polytetrafluoroethylene (ePTFE), polyethylene tetraphthlate (Dacron), polyurethane aliphatic polyesters, poly(amino acids), poly(propylene fumarate), copoly (ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and blends thereof.

Natural polymers suitable for use in the membranous tissue grafts include, but are not limited to, collagen, elastin, thrombin, fibronectin, starches, poly(amino acid), gelatin, alginate, pectin, fibrin, oxidized cellulose, chitin, chitosan, tropoelastin, hyaluronic acid, fibrin-based materials, collagen-based materials, hyaluronic acid-based materials, glycoprotein-based materials, cellulose-based materials, silks and combinations thereof.

A combination of one or more natural and/or synthetic materials can also be used. Particularly, any combination of the natural and/or synthetic materials disclosed in the preceding paragraphs can be used.

A "nerve graft" as used herein may generally refer to a graft implanted in a recipient to repair a damaged nerve or other tissue of a nervous system. A nerve graft can be made from a synthetic material, a natural material, or a combination thereof. Various materials used to prepare membranous tissue grafts indicated above can also be used in preparation of a nerve graft.

In an illustrative example embodiment, the membranous tissue graft may include porcine submucosa extracellular matrix ("ECM"). In some particular example embodiments, the tissue graft may include ECM in the form of a sheet that can be wrapped around a damaged tissue, such as a damaged nerve. An example of such a membranous tissue graft is modified AxoGuard Nerve Protector® described in Example 1 below.

In a further embodiment, the membranous tissue graft may include ECM in the form of a tube suitable for coaption of a severed nerve having a short gap or no gap, preferably, a gap of e.g., less than 5 mm between the severed stumps. An example of such a membranous tissue graft is a modified AxoGuard Nerve Connector® described in Example 2 below.

In another example embodiment, the membranous tissue graft may include a minimally processed human umbilical cord membrane that can be used as a resorbable soft tissue covering to, for example, separate tissue layers. An example of such a tissue graft is Avive Soft Tissue®, modified according to embodiments of the present disclosure.

In some embodiments, the membranous tissue graft (e.g., membranous tissue graft 102) may be used with tendon wrap and repair. For example, embodiments of the membranous tissue may strengthen a repair with a wrap, may support anti-adhesion, and/or may support de-tensioning. The membranous tissue graft may also be used with other types of tissue including a blood vessel, an intestine, a muscle (e.g., cardiac, skeletal, and smooth), nervous tissue (e.g., nerves, brain, and spinal cord), connective tissue, epithelial tissue, etc.

In certain embodiments, the membranous tissue grafts of the present disclosure can include one or more bioactive components that facilitate repair of a damaged nerve. Non-limiting examples of such bioactive compounds include heterologous or autologous growth factors, proteins (including matrix proteins), peptides, antibodies, enzymes, platelets, glycoproteins, hormones, cytokines, glycosaminoglycans, nucleic acids, analgesics, viruses, virus particles, cells, non-steroidal anti-inflammatories, cells and cellular components, or immunosuppressive therapies. In certain embodiments, the bioactive components suitable for use in the membranous tissue grafts of the present disclosure include interleukins, tissue inhibitors of metalloproteinases, epidermal growth factor, fibroblast growth factor, platelet derived growth factor, vascular endothelial growth factor, and transforming growth factor. In preferred embodiments, the bioactive growth factors comprise neurotrophic growth factors, such as brain-derived neurotrophic factor (BDNF), glial cell-derived neurotrophic factor (GDNF), neurotrophic factor (NGF), neutrophin-3 (NT-3), ciliary neurotrophic factor (CNTF), or leukemia inhibitory factor (LIF).

"Pre-made" as used herein may generally refer to the formation of an element or feature before or prior to use of the membranous tissue graft in connection with tissue repair. For example and in some embodiments, the one or more pre-made attachment points (e.g., one or more pre-made attachment points 104) may be formed or made during manufacturing of the membranous tissue graft. In this manner, one or more pre-made attachment points 104 (e.g., pre-made holes 106 and/or one or more pre-made etchings 108) may be formed or defined prior to the use of membranous tissue graft 102 in connection with tissue repair. In some embodiments, membranous tissue graft 102 may be manufactured without one or more pre-made attachment points 104 (e.g., pre-made holes 106 and/or pre-made etchings 108) but may have one or more pre-made attachment points 104 (e.g., pre-made holes 106 and/or one or more pre-made etchings 108) made prior to packaging and/or shipping of the membranous tissue graft. In this manner, membranous tissue graft 102 may comprise one or more pre-made attachment points 104 (e.g., pre-made holes 106 and/or one or more pre-made etchings 108) at the time membranous tissue graft 102 is provided to consumers.

"Suture holes" or "holes" as used herein may generally refer to preformed holes or cuts in a membranous tissue graft. For example, a surgeon can use the preformed suture holes (e.g., pre-made holes 106) to suture the tissue graft to a target site. Preformed suture holes (e.g., pre-made holes 106) may avoid the need for piercing the membranous tissue grafts during surgery and thus, may reduce the chances of damaging the suture needle with the possibility of subsequent tissue damage and allow any suture/needle combination to be used with equal ease. Referring also to the example of FIG. 2 and in some embodiments, suture holes (e.g., pre-made holes 106) can be any of a variety of shapes or combinations of shapes; for example, "+" sign (e.g., pre-made hole 202), "–" sign (e.g., pre-made hole 204), "x" sign (e.g., pre-made hole 206), a triangle (e.g., pre-made hole 208), a circle (e.g., pre-made hole 210), square, rectangle, semi-circle, wavy line, "/\/\/\/" design, etc.

In some embodiments, suture holes can be present towards the periphery of the membranous tissue grafts. In some embodiments, suture holes can be present throughout the entire periphery of the membranous tissue graft. Referring also to the example of FIG. 3 and in some embodiments, suture holes (e.g., pre-made holes 306) may be present along, for example, the periphery on opposite regions of the membranous tissue graft (e.g., membranous tissue graft 302). For example, if a tissue graft is rectangular, suture holes can be present along two opposite sides of the rectangle and absent on the other two sides of the rectangle. Similarly, if a tissue graft is circular, suture holes can be present along a portion of the circumference on opposite sides of the center.

Figure 3:
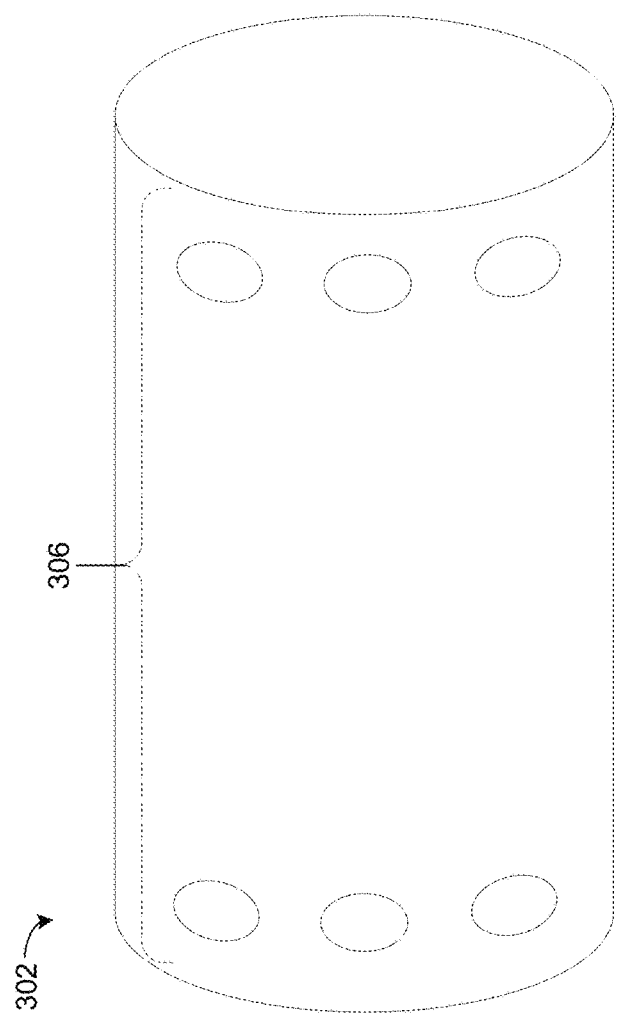
FIG. 3-6 show various configurations of one or more pre-made attachment points, particularly one or more pre-made holes or suture holes disposed on a membranous tissue graft consistent with embodiments of the present disclosure.

Referring again to the example of FIG. 3 and in some embodiments, the membranous tissue graft (e.g., membranous tissue graft 302) may be in the form of a tube and suture holes (e.g., pre-made holes 306) may be present along the edges at two ends of the tube. Such graft can be used in a nerve repair to connect a damaged or severed nerve and the two edges of the tube can be sutured to the two stumps of the damaged or severed nerve. While an example of using this example graft in nerve repair has been provided, it will be appreciated that the membranous tissue graft may be for any type of tissue repair. For example and in some embodiments, a membranous tissue graft may be used with tendon repair.

Figure 4:
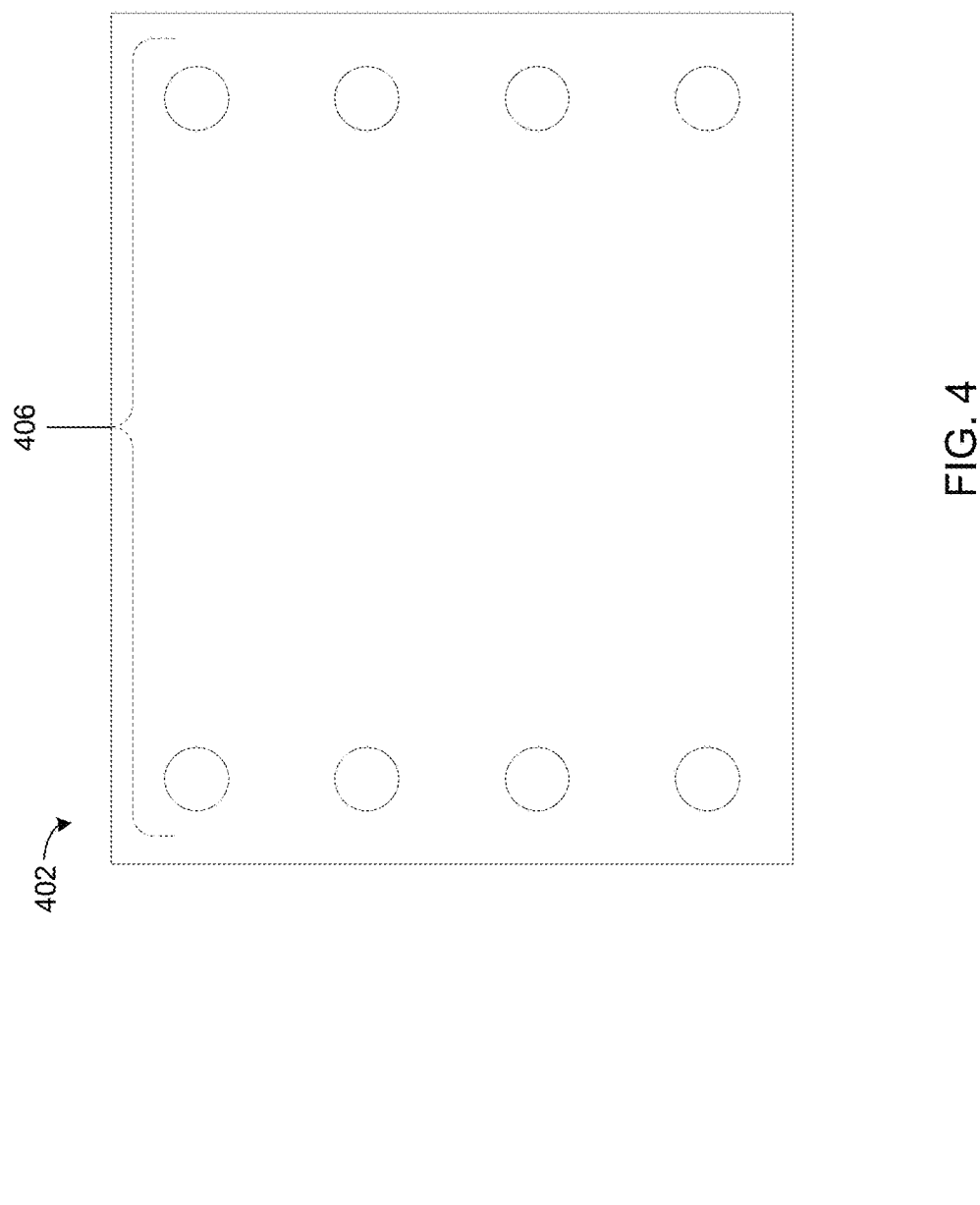
Figure 5:
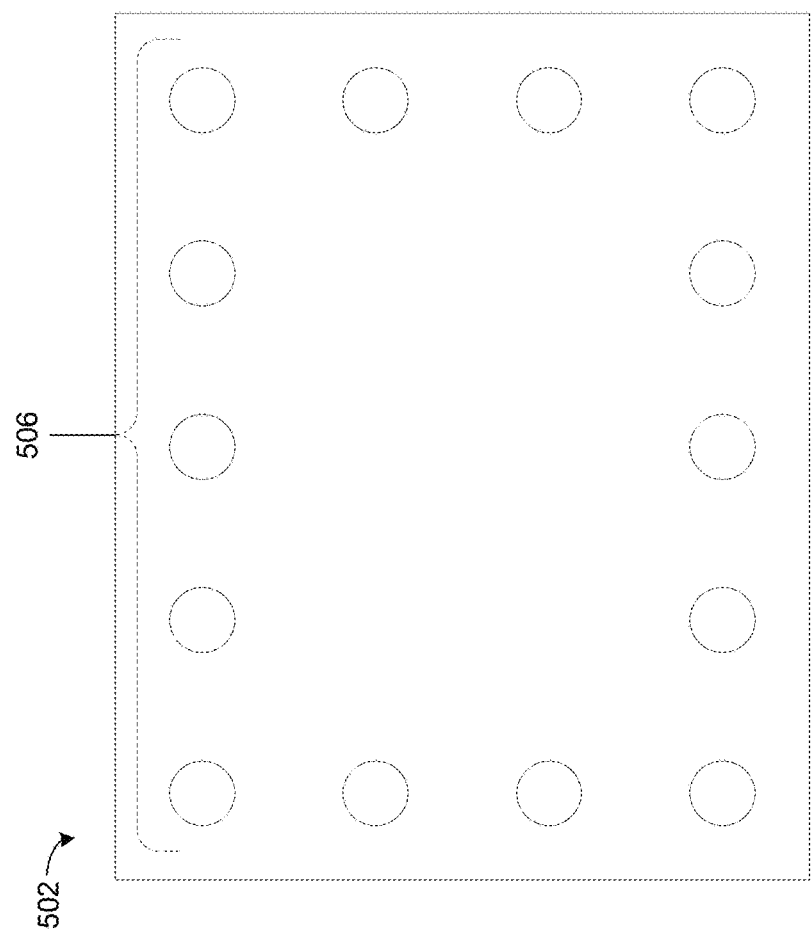
Figure 6:
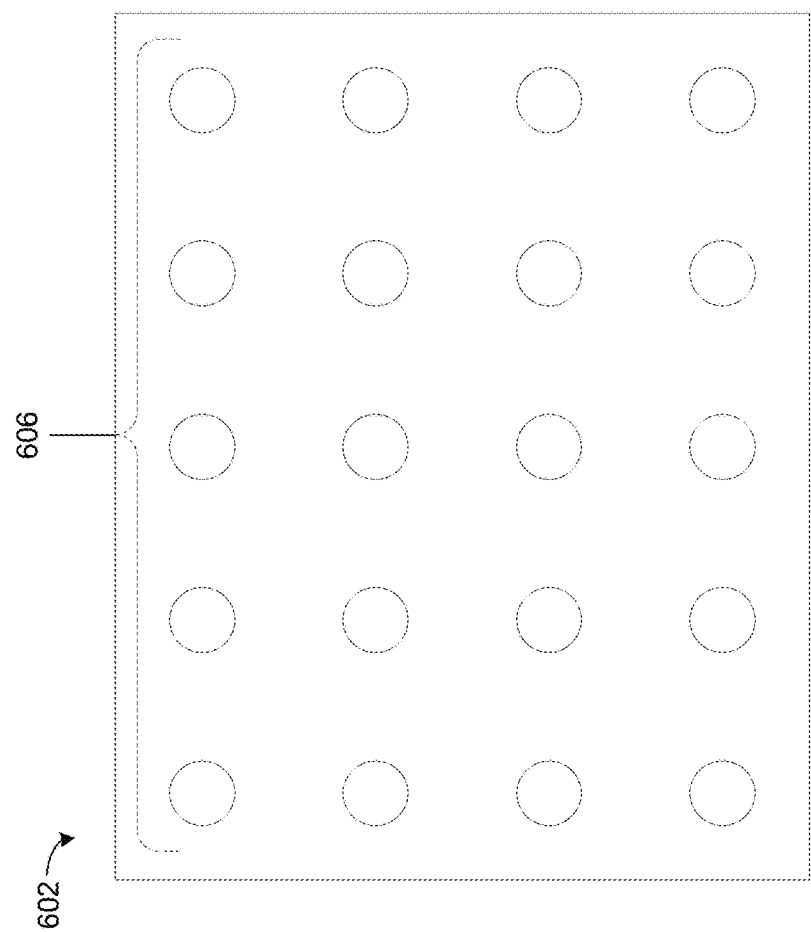

Referring also to the example of FIG. 4 and in some embodiments, membranous tissue graft (e.g., membranous tissue graft 402) may be rectangular in shape and suture holes (e.g., pre-made holes 406) may be present along the two opposite sides of the rectangle. Such membranous graft can be used in nerve repair by wrapping the severed or damaged nerve so that the sides of the rectangle having the suture holes encircle the severed portion of the nerve and these sides can be sutured to the two stumps of the severed nerve. While an example of wrapping a rectangular membranous tissue graft around a nerve has been provided, it will be appreciated that the membranous tissue graft may be wrapped around any tissue. For example and in some embodiments, a rectangular membranous tissue graft may be wrapped around a tendon. Referring also to the example of FIG. 5 and in some embodiments, suture holes (e.g., pre-made holes 506) can be present throughout the entire periphery of the rectangular membranous tissue graft (e.g., membranous tissue graft 502). Referring also to the example of FIG. 6 and in some embodiments, suture holes (e.g., pre-made holes 606) can be present throughout the entirety of the rectangular membranous tissue graft (e.g., membranous tissue graft 602). While FIG. 6 shows rows and columns of suture holes, it will be appreciated that the suture holes (e.g., pre-made holes 606) may be disposed in any pattern or configuration within the scope of the present disclosure.

In some embodiments, the suture holes may be present along the edge of the membranous tissue graft at a distance from the edge of: about 0.5 millimeters to about 10 millimeters; for example, about 1 millimeters to about 3 millimeters; and in some embodiments, about 1 millimeters.

However, it will be appreciated that the suture holes may be disposed at any distance from the edge of the membranous tissue graft within the scope of the present disclosure.

Referring again to the example of FIG. 1 and in some embodiments, "etching" as used herein may generally refer to a site or position in a membranous tissue graft where a portion of the material that forms the membranous tissue graft is removed to produce a region that has a different surface roughness than the surrounding material and is, therefore, visually differentiated from the rest of the membranous tissue graft. In some embodiments, a site of an etching (e.g., one or more pre-made etchings 108) may not contain a hole that passes through the membranous tissue graft. For example and in some embodiments, a surgeon can use the preformed etchings (e.g., one or more pre-made etchings 108) as guidance to appropriately place the graft onto a recipient tissue and/or to highlight the location of a hole used for suturing the graft. Additionally, etchings (e.g., one or more pre-made etchings 108) can be used as guidance marking to indicate other surgically relevant information, such as the distance between the nerve ends in a nerve conduit. Accordingly, the terms "etching" and "marking" may be used interchangeably within the scope of the present disclosure. In some embodiments, etchings (e.g., one or more pre-made etchings 108) can be any of a variety of shapes or combinations of shapes; for example, rectangle, triangle, semi-circle, etc. In certain embodiments, etchings or markings may be present or disposed towards the periphery of the tissue grafts. However, it will be appreciated that etchings may be disposed throughout the entire periphery of the tissue graft. Alternatively, etchings can be disposed or present only along the periphery on opposite sides of the tissue graft. For example, if a tissue graft is rectangular, etchings may be disposed or present along two opposite sides of the rectangle and absent along the other two sides of the rectangle. Similarly, if a tissue graft is circular or elliptical, etchings may be present along a portion of the circumference on opposite sides of the center.

Figure 7:
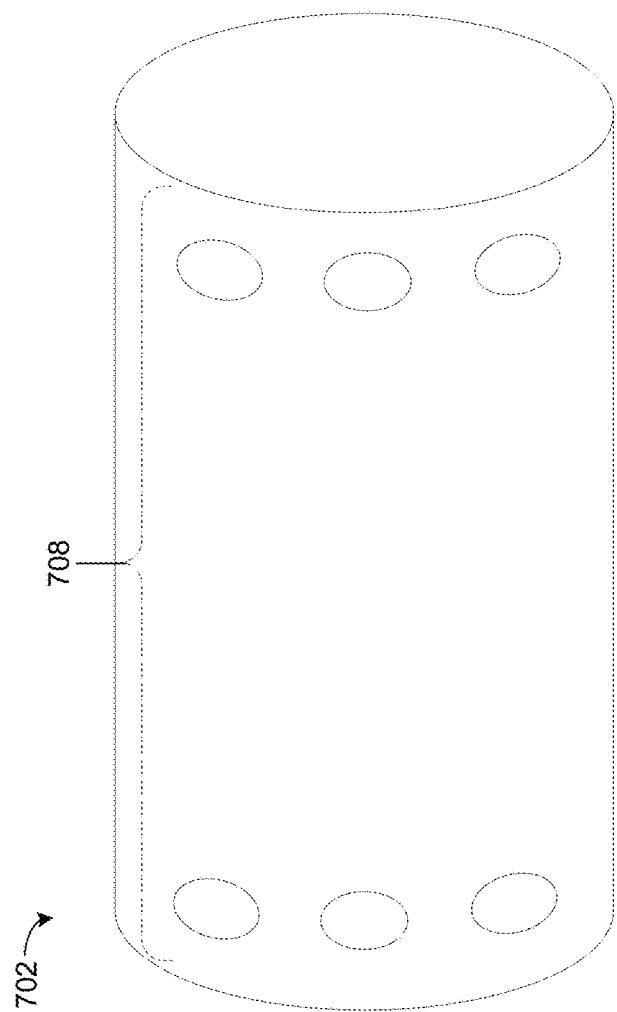
FIG. 7-10 show various configurations of one or more pre-made attachment points, particularly one or more pre-made etchings or markings disposed on a membranous tissue graft consistent with embodiments of the present disclosure.

Referring also to the example of FIG. 7 and in some embodiments, the membranous tissue graft (e.g., membranous tissue graft 702) may be in the form of a tube and etchings (e.g., one or more pre-made etchings 708) may be present or disposed along the edges at two ends of the tube. Such a membranous graft can be used in nerve repair to connect a damaged or severed nerve and the two edges of the tube can be sutured to the two stumps of the damaged or severed nerve.

Figure 8:
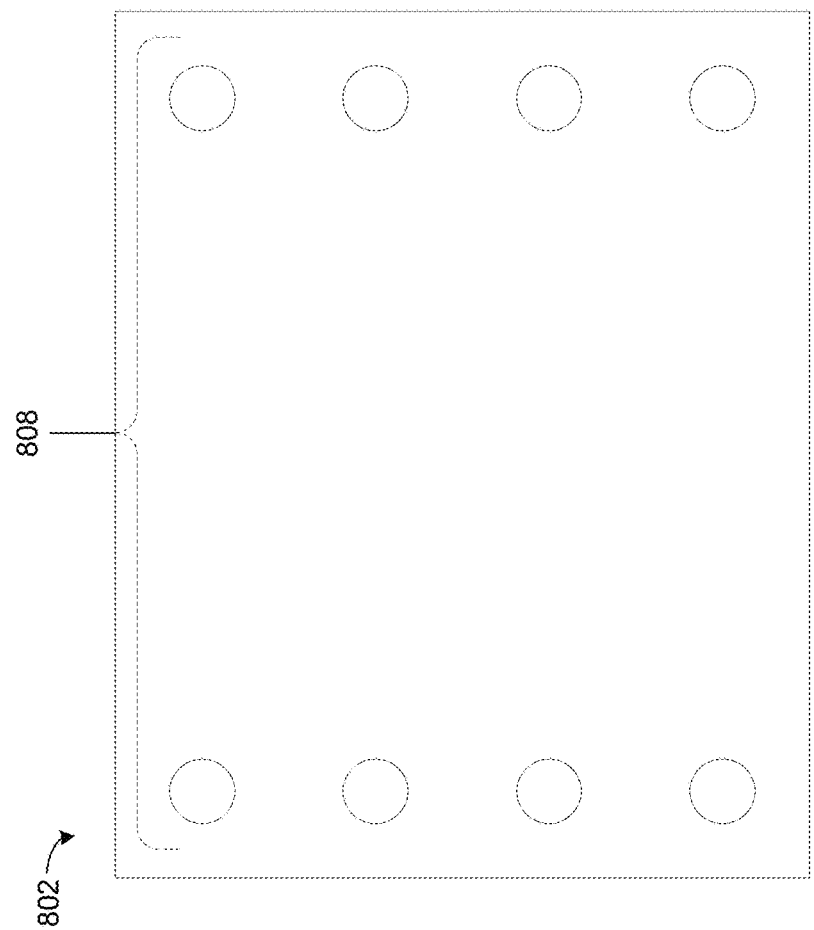
Figure 9:
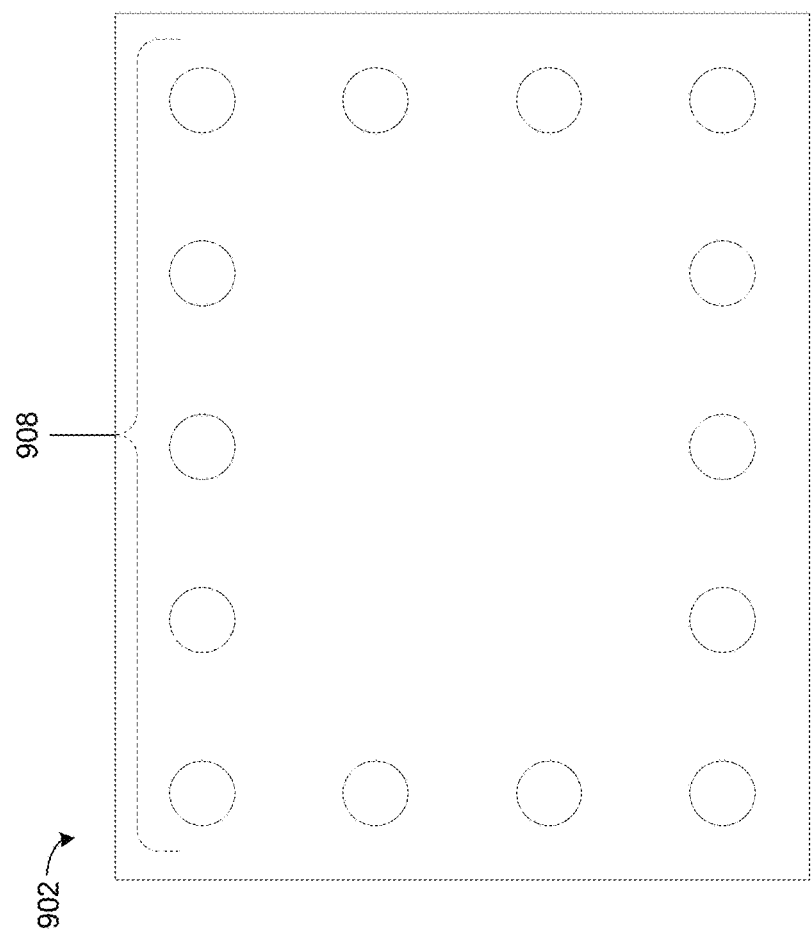
Figure 10:
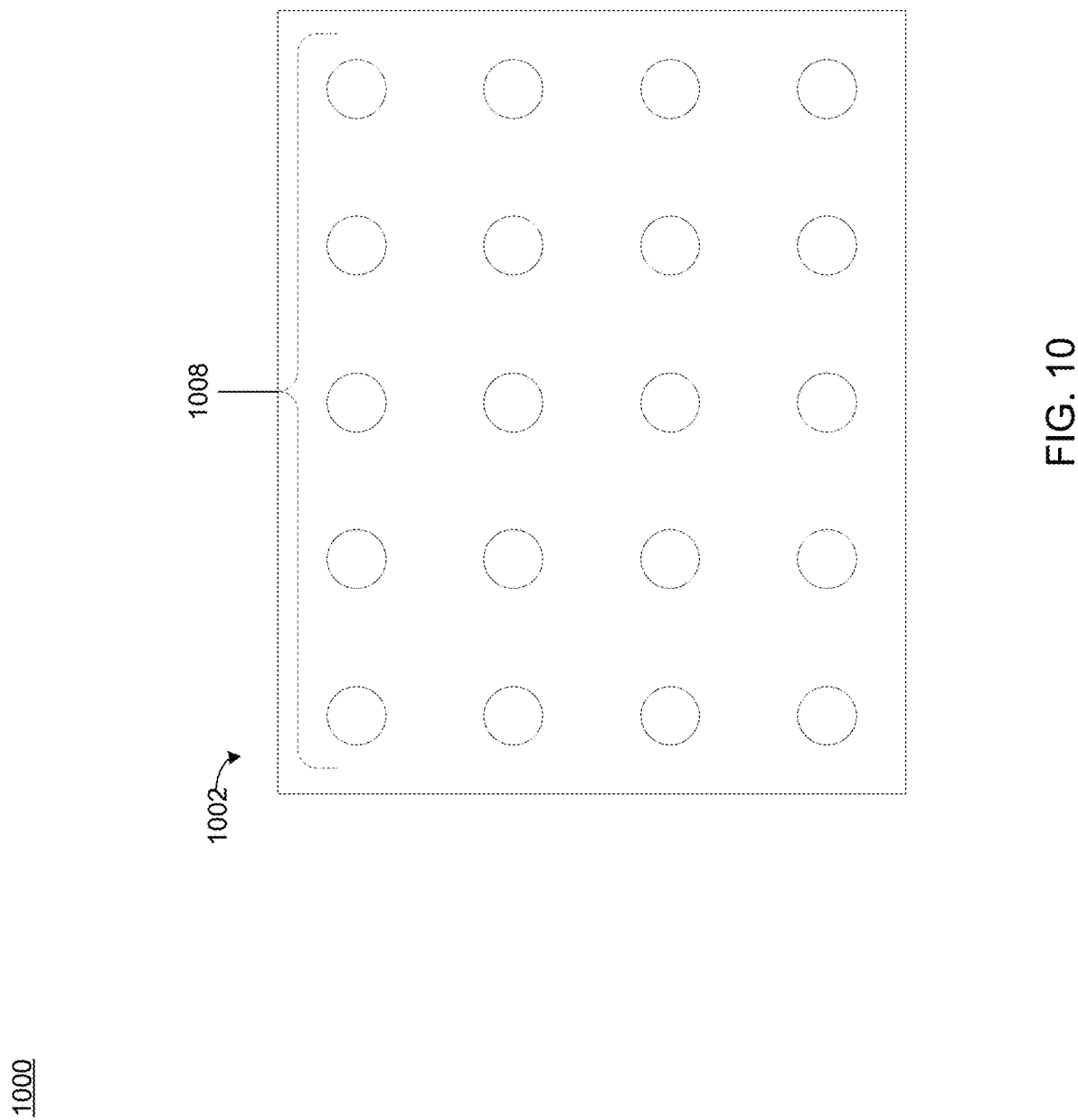

Referring also to the example of FIG. 8 and in some embodiments, the membranous tissue graft (e.g., membranous tissue graft 802) may be rectangular and etchings (e.g., one or more pre-made etchings 808) may be present along two opposite sides of the rectangle and absent along the other two sides. Such a graft can be used in nerve repair by wrapping the severed or damaged nerve so that the sides of the rectangle having the etchings encircle the nerve and these sides can be sutured to the two stumps of the severed nerve. While an example of wrapping a membranous tissue graft around a nerve has been provided, it will be appreciated that the membranous tissue graft may be wrapped around any tissue. For example and in some embodiments, a membranous tissue graft may be wrapped around a tendon. Referring also to the example of FIG. 9 and in some embodiments, etchings (e.g., pre-made etchings 908) can be present throughout the entire periphery of the rectangular membranous tissue graft (e.g., membranous tissue graft 902). Referring also to the example of FIG. 10 and in some embodiments, etchings (e.g., pre-made etchings 1008) can be present throughout the entirety of the rectangular membranous tissue graft (e.g., membranous tissue graft 1002). While FIG. 10 shows rows and columns of etchings, it will be appreciated that the etchings (e.g., pre-made etchings 1008) may be disposed in any pattern or configuration within the scope of the present disclosure.

In some embodiments, the etchings may be present along the edge of the membranous tissue graft as a ring at a distance from the edge of about 0.2 millimeters to about 1.5 millimeters, in some embodiments, about 0.5 millimeters to about 1.25 millimeters, and in some embodiments, about 1 millimeters. The etchings may be pre-formed in association with pre-made holes with the etched ring having a width between 50 microns and 1 millimeters, preferably, about 100 microns.

Figure 11:
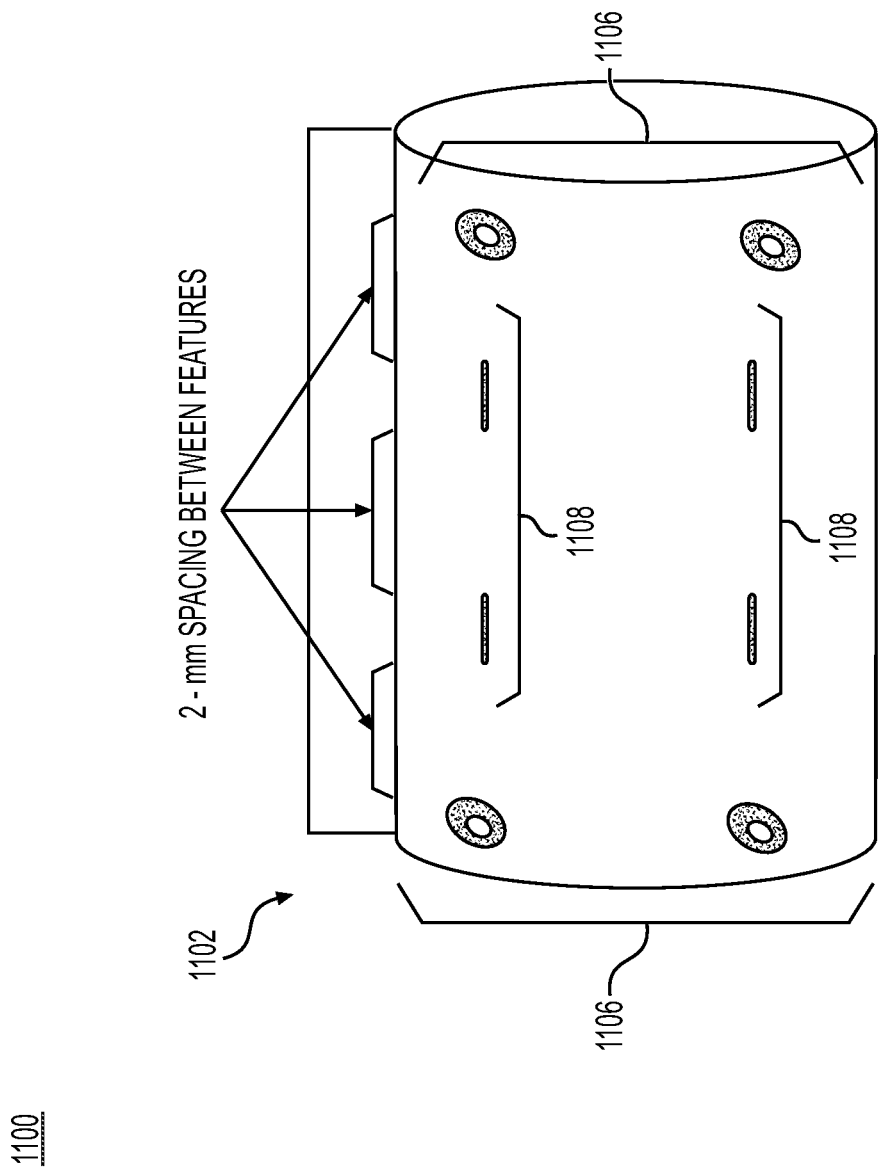
FIG. 11 shows an example implementation of the membranous tissue graft of the present disclosure in a nerve repair protector tissue graft.

Referring also to the example of FIG. 11 and in some embodiments, etched marks (e.g., pre-made etchings 1108) may also be present in the central portion of a membranous tissue graft (e.g., membranous tissue graft 1102) to orient and may guide the placement of the membranous tissue graft. One embodiment of an etch mark may include a "dash" approximately 200 microns by 1 millimeter which may be to assist a surgeon in placement of tissue at a measured distance within the membranous tissue graft. For example, the one or more etchings may assist a surgeon in placement of a nerve end within the membranous tissue graft at a measured distance within the membranous tissue graft (e.g., a measured distance within membranous tissue graft 1102). In some embodiments, the one or more markings may facilitate placement of multiple tissue ends at a measured distance from one another. For example, the one or more markings or etchings may assist a surgeon to determine when tissue or nerve ends are within e.g., 1 millimeter of each other within a membranous tissue graft (e.g., placement of tissue in each end at measured distance from each other within membranous tissue graft 1102). However, it will be appreciated that the one or more markings may be disposed to assist a surgeon when determining when multiple tissue ends are within any measure distance from one another and/or from an end of the membranous tissue graft.

In some embodiments, a membranous tissue graft may include one or more pre-made attachment points (e.g., one or more pre-made attachment points 104) which may include at least one of: one or more pre-made holes (e.g., one or more pre-made holes 106) and one or more etchings (e.g., one or more pre-made etchings 108). For example and referring again to the example of FIG. 11, membranous tissue graft 1102 (e.g., nerve repair protector tissue graft) may include one or more pre-made holes 1106 and one or more pre-made etchings 1108. In this manner, a surgeon may be guided by the orientation of one or more pre-made etchings 1108 when using one or more pre-made holes 1106 to repair tissue using membranous tissue graft 1102. In this example, a pre-defined spacing between pre-made attachment points of 2 millimeters is shown. However, it will be appreciated that any spacing may be used between pre-made attachment points (e.g., pre-made holes 1106 and/or pre-made etchings 108) within the scope of the present disclosure.

Referring also to the example of FIG. 12 and in some embodiments, membranous tissue graft 1202 (e.g., nerve repair connector tissue graft) may include one or more pre-made holes 1206. Referring again to the example of FIG. 2 and in some embodiments, etchings (e.g., etchings 212, 214, 216, 218, 220) can be placed around a suture hole (e.g., pre-made holes 202, 204, 206, 208, 210) to increase the visibility of the hole, for example, with a ring of etched area that surrounds a hole. In such embodiments, a surgeon can suture the membranous tissue graft by suturing through the hole, with improved visibility of the hole indicated by the etching. Alternately, a reinforced area comprising a thickened region of the material (e.g., reinforced areas 222, 224, 226, 228, 230) that forms the tissue graft, or an alternate material, can be used to provide the visual contrast in a similar manner. The reinforced area (e.g., reinforced areas 222, 224, 226, 228, 230) can also include a supporting material, such as glue or rings of supporting fibers or wires that surround the hole. The reinforced area can be any shape, such as, a circle, oval, ellipse, square, triangle, rectangle, etc. that surrounds the hole.

In some embodiments, the etchings and/or suture holes may include additional markings that further increase visibility of the etchings and/or suture holes. The markings can be placed and designed in a manner that indicates orientation of the membranous tissue graft. For example, markings in a specific asymmetric area of a rectangular membranous tissue graft can be used to indicate two surfaces of the membranous tissue graft because of the asymmetric positioning of the markings.

In some embodiments, the etchings and/or suture holes in the membranous tissue grafts of the present disclosure may facilitate suturing of the membranous tissue grafts to an injured tissue, such as an injured nerve. Accordingly, methods of using the membranous tissue grafts of the present disclosure are also described, for example, methods of repairing a damaged tissue, such as a damaged or severed nerve or a damaged tendon.

In some example embodiments, the present disclosure may provide methods of repairing injured nerves, particularly, damaged or severed nerves that have no gap or a gap of e.g., less than about 5 mm between the severed nerve stumps. In these methods, a membranous tissue graft in the form of a tube may be sutured to the severed stumps of the injured nerve. Implantation of such a tissue graft may allow the body's natural healing process to repair the severed nerve by isolating and protecting the severed nerve during the healing process. For example, the patient's cells can incorporate into the extracellular matrix to remodel and form a tissue similar to the nerve epineurium.

In certain other cases of nerve injuries where the injured nerves have no gap or a small gap, for example, less than about 5 mm, a membranous tissue graft in the form of a rectangle may be wrapped around the injured nerve and such membrane is sutured to the injured nerve.

Implantation of a membranous tissue graft of the present disclosure may protect injured nerves and reinforces the nerve reconstruction. The suture holes may help in the use of any suture especially when the suture needle may not be mechanically appropriate for the membranous tissue graft. Designed to protect and isolate, the membranous tissue grafts may separate and protect the injured nerve from the surrounding tissues during the healing process. The patient's cells incorporate into the minimally processed extracellular matrix to remodel and form a tissue similar to the nerve epineurium.

Definitions

As used herein, the singular forms "a", "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," "consisting essentially of" "consists essentially of," "consisting," and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. In the context of the size of various parameters of the membranous tissue grafts of the present disclosure where the term "about" is used, these parameters are within a variation (error range) of 0-10% around the stated value (X±10%).

In the present disclosure, ranges are stated in shorthand so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

When ranges are used herein, combinations and subcombinations of ranges (e.g., subranges within the disclosed range), specific embodiments therein are intended to be explicitly included.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing embodiments of the present disclosure. These examples should not be construed as limiting.

Example 1

AxoGuard Nerve Connector® (AxoGen, Inc.) modified according to embodiments of the present disclosure. Referring again to the example of FIG. 12 and in some embodiments, AxoGuard Nerve Connector® may provide minimally processed porcine extracellular matrix for connector-assisted coaptation of severed or damaged nerves. Certain aspects of AxoGuard Nerve Connector® are described in the brochure entitled "Nerve Repair Solution," AxoGen Inc. (2015). This brochure is incorporated herein in its entirety.

In this Example, the AxoGuard Nerve Connector® may be modified according to embodiments of the present disclosure by providing one or more attachment points (e.g., etching and/or suture holes). Such modified AxoGuard Nerve Connector® may be suitable for repair of severed nerves, such as severed nerves that have no gap or a gap of e.g., less than about 5 mm between the severed nerve stumps. The modified AxoGuard Nerve Connector® may be in the form of a tube that is designed for implantation on to an as injured nerve. The modified AxoGuard Nerve Connector® can have a dimension of 1.5 mm×10 mm, 2 mm×10 mm, 3 mm×10 mm, 4 mm×10 mm, 5 mm×10 mm, 6 mm×10 mm, 7 mm×10 mm, 1.5 mm×15 mm, 2 mm×15 mm, 3 mm×15 mm, 4 mm×15 mm, 5 mm×15 mm, 6 mm×15 mm, or 7 mm×15 mm. However, it will be appreciated that the modified AxoGuard Nerve Connector® can have any dimensions within the scope of the present disclosure.

In some embodiments, the modified AxoGuard Nerve Connector® can have etching and/or suture holes along the edges at the two ends of the tube.

Example 2

AxoGuard Nerve Protector® (AxoGen, Inc.) modified according to embodiments of the present disclosure. AxoGuard Nerve Protector® may provide minimally processed porcine extracellular matrix for wrapping or protecting severed or damaged nerve. Certain aspects of AxoGuard Nerve Protector® are described in the brochure entitled "Nerve Repair Solution," AxoGen Inc. (2015). This brochure is incorporated herein in its entirety.

Referring again to the example of FIG. 11 and in this Example, the AxoGuard Nerve Protector® may be modified according to embodiments of the present disclosure by providing one or more attachment points (e.g., etching and/or suture holes). Such modified AxoGuard Nerve Protector® may be suitable for wrapping and protecting severed nerves, such as severed nerves that have no gap or a gap of less than about 5 mm between the severed nerve stumps. The modified AxoGuard Nerve Protector® may be in the form of a rectangle which when wrapped around a damaged or severed nerve produces a tube having a size of 2 mm×20 mm, 3.5 mm×20 mm, 5 mm×20 mm, 7 mm×20 mm, 10 mm×20 mm, 3.5 mm×40 mm, 5 mm×40 mm, 7 mm×40 mm, or 10 mm×40 mm. However, it will be appreciated that the modified AxoGuard Nerve Protector® can have any dimensions within the scope of the present disclosure.

The modified AxoGuard Nerve Connector® can have etching or suture holes along the two sides that encircle the nerves and form two ends of the tube when the modified AxoGuard Nerve Connector® is wrapped around a severed nerve or other tissue.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

We claim:

1. A membranous tissue graft with one or more pre-made attachment points, wherein the one or more pre-made attachment points include one or more etchings, and wherein the one or more etchings are configured for use to:
   increase visibility of the one or more pre-made attachment points;
   guide placement of the membranous tissue graft onto recipient tissue;
   determine an orientation of the membranous tissue graft;
   assist with placement of one or more nerve ends at a measured distance within the membranous tissue graft; and/or
   facilitate placement of multiple nerve ends at a measured distance from one another within the membranous tissue graft.

2. The membranous tissue graft of claim 1, having a thickness of between 25 microns and 3 millimeters.

3. The membranous tissue graft of claim 1, comprising a natural material.

4. The membranous tissue graft of claim 3, wherein the natural material is selected from porcine small intestine submucosa, amniotic/chorionic membrane, reconstituted denatured collagen, collagen, elastin, thrombin, fibronectin, starches, poly(amino acid), gelatin, alginate, pectin, fibrin, oxidized cellulose, chitin, chitosan, tropoelastin, hyaluronic acid, fibrin-based materials, collagen-based materials, hyaluronic acid-based materials, glycoprotein-based materials, cellulose-based materials, silks, and combinations thereof.

5. The membranous tissue graft of claim 1, comprising a synthetic material.

6. The membranous tissue graft of claim 5, wherein the synthetic material is selected from silicone, expanded polytetrafluoroethylene (ePTFE), polyethylene tetraphthlate (Dacron), polyurethane aliphatic polyesters, poly(amino acids), poly(propylene fumarate), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and blends thereof.

7. The membranous tissue graft of claim 1, comprising one or more bioactive components that facilitate repair of a damaged tissue.

8. The membranous tissue graft of claim 1, wherein the one or more pre-made attachment points further include one or more pre-made suture holes or cuts.

9. The membranous tissue graft of claim 8, wherein the membranous tissue graft is in the form of a tube and the one or more suture holes or cuts are disposed along edges at two ends of the tube.

10. The membranous tissue graft of claim 8, wherein the membranous tissue graft is rectangular and the one or more suture holes or cuts are disposed along two opposite sides of the rectangular membranous tissue graft and are absent along the other two sides.

11. The membranous tissue graft of claim 8, wherein the one or more suture holes or cuts are disposed along the edge of the tissue graft at a distance from the edge of about 0.5 millimeters to about 10 millimeters.

12. The membranous tissue graft of claim 8, wherein the one or more etchings are formed around the one or more suture holes or cuts, respectively.

13. The membranous tissue graft of claim 1, wherein the one or more pre-made attachment points are disposed towards a periphery of the membranous tissue graft.

14. The membranous tissue graft of claim 1, wherein the membranous tissue graft is in the form of a tube and the one or more pre-made attachment points are disposed along edges at two ends of the tube.

15. The membranous tissue graft of claim 1, wherein the membranous tissue graft is rectangular and the one or more pre-made attachment points are disposed along two opposite sides of the rectangular membranous tissue graft and are absent along the other two sides.

16. The membranous tissue graft of claim 1, wherein the one or more pre-made attachment points are disposed along the edge of the membranous tissue graft at a distance from the edge of about 0.5 millimeters to about 10 millimeters.

17. The membranous tissue graft of claim 1, wherein the membranous tissue graft is in the form of a tube or a sheet, wherein the one or more pre-made attachment points also include one or more suture holes or cuts, and wherein the one or more etchings or the one or more suture holes or cuts are disposed at one or both of a periphery or a central region of the tube or the sheet.

18. The membranous tissue graft of claim 1, wherein the one or more etchings include more than one etching, and wherein at least one etching of the more than one etching is different in at least one of shape or size from another etching of the more than one etching.

19. The membranous tissue graft of claim 1, wherein the graft comprises one or more etchings on an exterior of the graft.

20. A method comprising implanting a membranous tissue graft comprising one or more pre-made attachment points, wherein the one or more pre-made attachment points include one or more etchings, and wherein the method further comprises one or more of:
   using the one or more etchings to determine an orientation of the membranous tissue graft;
   using the one or more etchings to assist with placement of one or more nerve ends at a measured distance within the membranous tissue graft; and/or
   using the one or more etchings to facilitate placement of multiple nerve ends at a measured distance from one another within the membranous tissue graft.

21. The method of claim 20, wherein implanting the membranous tissue graft includes positioning the membranous tissue graft so that the membranous tissue graft at least partially houses two nerve ends, the nerve ends being opposed to one another, and wherein a gap between the two nerve ends is in the range of about 0 millimeters to about 5 millimeters.

\* \* \* \* \*

UNITED STATES PATENT AND TRADEMARK OFFICE
CERTIFICATE OF CORRECTION

PATENT NO. : 11,166,800 B2
APPLICATION NO. : 16/381860
DATED : November 9, 2021
INVENTOR(S) : Curt Andrew Deister, Jonathan Andrew Tinnemeyer and Kirk Michael Grayam Page 1 of 1

It is certified that error appears in the above-identified patent and that said Letters Patent is hereby corrected as shown below:

In the Claims

In Claim 6, Column 12, Line 22, please delete "tetraphthlate" and insert --terephthalate--.

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*